United States Patent [19]

Rapoport et al.

[11] 4,060,558

[45] Nov. 29, 1977

[54] PROCESS FOR PREPARING 3-ALKYL-4-ALKOXY-1-NAPHTHOLS

[75] Inventors: Henry Rapoport, Berkeley; Clinton D. Snyder, Monte Sereno, both of Calif.

[73] Assignee: The Regents of the University of California, Berkeley, Calif.

[21] Appl. No.: 620,288

[22] Filed: Oct. 7, 1975

Related U.S. Application Data

[62] Division of Ser. No. 565,472, April 7, 1975, Pat. No. 3,948,958.

[51] Int. Cl.$^2$ .............................................. C07C 41/00
[52] U.S. Cl. ................................................ 260/613 D
[58] Field of Search ..................................... 260/613 D

[56] References Cited

U.S. PATENT DOCUMENTS

| 487,204 | 11/1892 | Ach | 260/613 D X |
| 1,792,716 | 2/1931 | Stockelbach | 260/613 D X |
| 2,807,643 | 9/1957 | Hartley | 260/613 D X |

FOREIGN PATENT DOCUMENTS

| 14,628 | 8/1967 | Japan | 260/613 D |

Primary Examiner—Bernard Helfin
Attorney, Agent, or Firm—Bernard & Brown

[57] ABSTRACT

3-Prenyl-substituted-2-alkyl menaquinones are made by reacting an alkali metal salt of a 3-alkyl-4-alkoxy or aralkoxy-1-naphthol with a prenyl halide, and oxidizing the resulting 2-prenyl-3-alkyl-4-alkoxy or aralkoxy-1-naphthol to the corresponding 3-prenyl-substituted-2-alkyl menaquinone. There is also disclosed a procedure for making the alkali metal salts involving the preparation of an ether-ester and hydrogenolysis.

4 Claims, No Drawings

PROCESS FOR PREPARING 3-ALKYL-4-ALKOXY-1-NAPHTHOLS

This is a division, of application Ser No. 565,472, filed Apr. 7, 1975 and now U.S. Pat. No. 3,948,958.

This invention relates to a method of synthesizing menaquinones, and particularly 3-prenyl-2-alkyl menaquinones. The invention includes the preparation of 3-alkyl-4-alkoxy or aralkoxy-1-naphthols and their alkali metal salts, the latter being novel compounds. According to the invention, these alkali metal salts can be reacted with a prenyl halide to prepare the corresponding 2-prenyl-3-alkyl-4-alkoxy or aralkoxy-1-naphthols, which can be oxidized to the corresponding 3-prenyl-2-alkyl menaquinones. It is a further aspect of the invention that the oxidation is advantageously conducted by the use of ferric ions.

The 3-prenyl-2-alkyl menaquinones prepared by this invention have the structural formula:

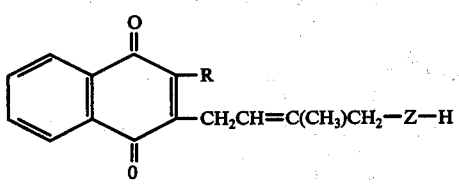

wherein R is alkyl, for instance, lower alkyl, say of 1 to about 4 or 8 carbon atoms, preferably methyl, and wherein Z is $[CH_2CH=C(CH_3)CH_2]_m[CH_2CH_2CH(CH_3)CH_2]_n$, or combinations thereof, and in which each of $m$ and $n$, and their sum, may be 0 to about 25 or more, and frequently, each of $m$ and $n$, and their sum, are 0 or 1 to about 9 or 12. For convenience, these compounds are sometimes hereinafter referred to as the MK Compounds. These compounds have heretofore been designated as being in the vitamin K series, see U.S. Pat. No. 2,348,037, and can be administered to red-blooded animals in the usual manner as vitamin K compounds to combat bleeding. The MK Compounds wherein the prenyl component at the 3-position carbon has the trans configuration exhibit the greatest anti-hemorrhagic activity, especially when R is methyl. By the method of this invention, the MK Compounds can be prepared without undue degradation of the prenyl substituent or reactant, and the stereoconfiguration at the olefinic bond in the prenyl halide reactant or prenyl substituent can be maintained.

There have been numerous attempts to prepare prenyl-substituted menaquinones, but difficulties have been encountered in terms of undesirably low yields, maintenance of the stereoconfiguration of the prenyl structure, instability of the prenyl reactant in the case of using it as an allylic alcohol, and occurrence of side reactions such as branched chain isomerization or chromanol cyclization. For example, an approach to the synthesis of MK Compounds which has been suggested involved the condensation of 2-methyl-1,4-naphthoquinol with an allylic alcohol in the presence of an acidic catalyst such as boron trifluoride etherate. The resulting menaquinol can be converted by mild oxidation to the corresponding menaquinone. This suggested route for synthesizing the MK Compounds has not, however, proven to be entirely satisfactory in that under the acidic conditions employed for alkylation, the allylic alcohol is unstable, and thus the yields of MK Compounds based on the allylic alcohol reactant are low. Another approach which has been suggested is through the use of N-sulfinylamine ester of the prenyl component as the reactant to prepare MK Compounds from, for instance, 2-methyl-1,4-naphthoquinol. This reaction, however, proceeds with poor yields of MK Compounds.

By the present invention, it has been found that 3-prenyl-2-alkyl menaquinones can be made without encountering to undesirable extents the difficulties previously experienced in such syntheses as noted above. In our studies, we endeavored to prepare the prenylated products by the alkylation of the monopotassium salt of 2-methyl-1,4-naphthoquinol which was an approach that had been used by others using phytyl bromide as the alkylating agent. Difficulty was experienced in preparing the monopotassium salt, and a low yield of the desired product was obtained in the alkylation when using geranyl bromide as the alkylating agent.

In the present invention, the preparation of the 3-prenyl-2-alkyl menaquinones has been found to proceed satisfactorily by reaction of a prenyl halide alkylating agent with an alkali metal salt of a 3-alkyl-4-alkoxy or aralkoxy-1-naphthol. The alkali metal salts of the 3-alkyl-4-alkoxy or aralkoxy-1-naphthols are believed to be new compositions of matter. A further aspect of the present invention is the preparation of the 3-alkyl-4-alkoxy or aralkoxy-1-naphthols by a synthesis route which was devised when efforts to prepare these materials by other methods proved disadvantageous.

The efficient preparation of the monoether, 3-alkyl-4-alkoxy or aralkoxy-1-naphthol proved to be more complex than initially assumed. Its preparation had been described in Japanese patent application No. 14,628 (1967), Chem. Abs., Vol. 68, 49351h, 1968, but by using an acetate reactant prepared in only low yield. In order to improve on this result, we first examined the possibility of synthesizing the monomethyl ether through either selective methylation or demethylation processes. Methylation of 2-methyl-1,4-naphthoquinol with either a limiting amount of methyl iodide or limiting amount of base, yielded principally dimethylation, and the monomethyl ether fraction that was isolated contained a preponderance of the undesired 4-methoxy-2-methyl-1-naphthol. Direct etherification of a naphthoquinol with methanolic HCl gave monoalkylation, but again, when applied to 2-methyl-1,4-naphthoquinol, there is obtained exclusively 4-methoxy-2-methyl-1-naphthol.

Selectivity in demethylation of various aryl methyl ethers has been obtained with thioethoxide; however, when either this nucleophile or iodide was applied to 2-methyl-1,4-dimethoxy naphthalene, a mixture of monoethers was obtained with an unfavorable distribution of only one part of 3-methyl-4-methoxy-1-naphthol to four parts of the undesired 4-methoxy-2-methyl-1-naphthol. Clearly, a steric effect from the adjacent 2-methyl substituent is insufficient to effect any selectivity in the site of nucleophilic attack. Alternatively, both methylation and demethylation conditions may be reversible so that thermodynamic control prevails, in which case, 4-methoxy-2-methyl-1-naphthol would be expected to be more stable (less peri-interaction) thus dooming a facile preparation of 3-methyl-4-methoxy-1-naphthol by these methods.

A way of preparing the 3-alkyl-4-alkoxy or aralkoxy-1-naphthols in improved yields has been devised by this invention. This method utilizes as a starting material 2-alkyl-1,4-naphthoquinol-1-acyl having the formula:

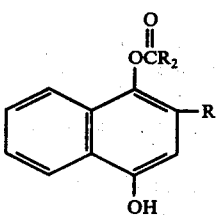

wherein R and $R_2$ are alkyl, especially lower alkyl, say of 1 to about 4 or 8 carbon atoms, preferably methyl. The 4-position of this reactant is then masked as a benzyl-type aralkyl ether, e.g., benzyl, of, for example, 7 to about 10 or more carbon atoms, having only one carbon atom between the ring structures. The resulting compounds have the formula

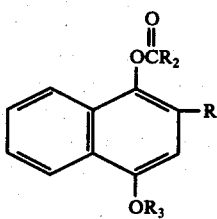

wherein $R_3$ is a benzyl-type aralkyl group, and R and $R_2$ are as defined above. The acyl group,

can be removed by hydrolysis from the latter products to provide the corresponding naphthols of the formula:

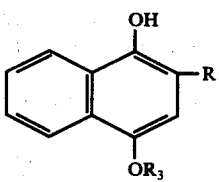

wherein R and $R_3$ are as defined bove. The free phenol group of these compounds can be alkylated to the corresponding compounds:

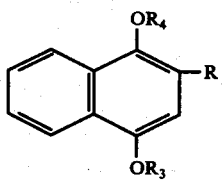

wherein $R_4$ is alkyl, for example lower alkyl, say of 1 to about 4 or 8 carbon atoms, preferably methyl, or, less preferably, $R_4$ may be aralkyl of 8 to 10 or 12 carbon atoms with at least 2 carbon atoms being in the chain directly between the fused ring and the monocyclic aryl group of the aralkyl, e.g., phenethyl. The benzyl-type aralkyl ether group, $-OR_3$, of these compounds can then be converted by hydrogenolysis to provide good yields of the corresponding 3-alkyl-4-alkoxy or aralkoxy-1-naphthols which are readily converted to the corresponding alkali metal salts, especially the sodium and potassium salts, having the formula:

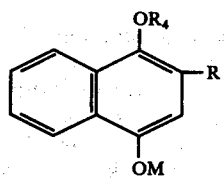

wherein M is alkali metal such as sodium or potassium, preferably potassium, and R and $R_4$ are as defined above.

The synthesis of the 3-prenylated menaquinones can be accomplished by alkylation of the corresponding foregoing described alkali metal salts of the 3-alkyl-4-alkoxy or aralkoxy-1-naphthols by the use of a corresponding prenyl halide alkylating agent. The desired 1-naphthol products of this reaction have the formula:

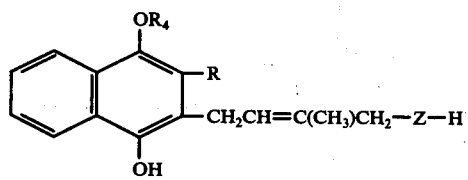

wherein R, $R_4$ and Z are as described above. The alkylated products can be converted to the corresponding 3-prenyl-2-alkyl menaquinones by oxidation.

In the synthesis of this invention, the 2-alkyl-1,4-naphthoquinol-1-acyl reactant can be made by selective hydrolysis of the corresponding diacyl compound according to the procedure described by B. R. Baker et al., J. Amer. Chem. Soc., Vol. 64, 1096 (1942). Conversion of this reactant to the corresponding 4-benzyl-type aralkyl ether-ester can be accomplished by the use of a benzyl-type aralkyl halide, e.g., of 7 to about 10 or more carbon atoms, such as a chloride or bromide, preferably the latter. We advantageously employ an excess of the aralkyl halide reactant. The reaction can be conducted in the presence of a basic material to neutralize released hydrogen halide, and these basic materials include the alkali metal bases or salts, especially those of sodium or potassium, preferably the latter, as in the case of potassium carbonate. The basic material can be used in excess. The reaction proceeds at elevated temperatures, and the reaction system is generally essentially anhydrous. The reaction is preferably conducted under an inert atmosphere, e.g., nitrogen. The reaction temperature may, for example, be in the range of about 50° to 100° C., preferably about 50° to 60° C. A liquid organic solvent is generally present in the reaction in an amount sufficient to dissolve the organic reactants, and oxygen-containing solvents such as ketones can readily be used.

The 4-aralkyl ether-ester can be hydrolyzed to a 2-alkyl-4-aralkoxyl-1-naphthol in a basic aqueous medium in which a liquid organic solvent may be present in an amount sufficient to dissolve the organic reactant. Oxygen-containing solvents can be used, such as an alcohol, e.g., a lower alkanol. The basic component is preferably an alkali metal hydroxide, especially potassium hydroxide. This reaction is generally conducted at elevated temperatures, e.g., up to about 110° C., but higher temperatures could be employed if desired. Advantageously, the reaction is conducted in an inert atmosphere such as nitrogen.

Alkylation of the 1-position of the 2-alkyl-4-aralkoxy-1-naphthol can be accomplished by the use of the corresponding alkyl or aralkyl halide, preferably in excess. The product of this invention is a 1-alkoxy or aralkoxy-2-alkyl-4-aralkoxynaphthalene. Alkyl or aralkyl iodides, especially methyl iodide, are preferred alkylating agents, and this reaction can be conducted in a basic medium. The basic reagent may be an alkali metal base or salt, say of sodium or potassium, especially potassium as in the case of potassium carbonate. This reaction proceeds at elevated temperatures, e.g., about 50° to 100° C., preferably about 50° to 60° C. The reaction is generally conducted in the presence of a sufficient amount of liquid organic solvent such as an oxygen-containing material. Ketones are quite satisfactory, especially acetone. We prefer that the reaction system be essentially anhydrous and that the reaction proceed under an inert atmosphere, such as nitrogen.

Hydrogenolysis can be used to convert the 1-alkoxy or aralkoxy-2-alkyl-4-aralkoxynaphthalene to the corresponding 4-alkoxy or aralkoxy-3-alkyl-1-naphthol. The hydrogenolysis proceeds readily in the presence of solid catalysts, and under mild conditions. Thus, with platinum group metal catalysts, the reaction can be conducted at room temperature and atmospheric pressure, although elevated temperatures and pressures may be used. Hydrogen is generally provided in excess and, if desired, in admixture with an inert gas such as nitrogen and in the essential absence of molecular oxygen. The reaction can be conducted in the presence of a sufficient amount of a liquid organic solvent to dissolve the organic reactant. Such solvents may be oxygen-containing materials such as esters, as in the case of ethyl acetate. Suitable reaction temperatures are about 15° to 100° C., preferably about 20° to 60° C., and the pressure may be up to about 10 atmospheres or more.

The 4-alkoxy or aralkoxy-3-alkyl-1-naphthol can be converted to the corresponding alkali metal salt or naphthate by reaction with a suitable alkali metal component such as an alkali metal hydride, hydroxide, amide, or alkoxide, e.g., a methoxide. A liquid organic solvent should be used in the reaction system in an amount sufficient to dissolve the organic reactants. Suitable solvents include aromatic hydrocarbons such as benzene, toluene, xylene, and the like. Preferably, the solvent is present in an amount sufficient to dissolve the reactants and products, but is not in such large amounts that recovery of the product is unduly hindered. Often, the solvent is provided in a weight ratio to naphthalenic component of about 1:1 to 1000:1, preferably 25:1 to 500:1. The reaction is desirably maintained under anhydrous conditions. The solvent may advantageously be dried or distilled from sodium to insure anhydrous conditions. The temperature of the reaction medium is usually elevated, for instance up to about 150° C. or more, preferably about 40° or 60° C. to 120° or 130° C.

The reaction with the alkali metal component evolves hydrogen, and to facilitate the reaction, the evolved hydrogen may be removed from the reaction vessel. The reaction may be conducted at subatmospheric pressure to enhance the removal of hydrogen. In order to insure anhydrous conditions, an inert gas atmosphere such as nitrogen may be employed. Desirably, oxygen is excluded from the reaction. Potassium hydride in toluene has been found to react more readily and at lower temperatures than sodium hydride. If sodium hydride is to be employed as the reactant, the use of higher temperatures may be desirable. The temperature is generally not substantially above the boiling point of the reaction mixture at the condition of the reaction. The reaction may be permitted to run until the evolution of hydrogen ceases, and often this occurs after about 0.5 to 50 hours.

In the invention, the alkali metal salt of the 3-alkyl-4-alkoxy or aralkoxy-1-naphthol is reacted with a prenyl-type component of the formula

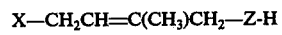

wherein X is halogen, preferably having an atomic number from 17 to 35, i.e., chlorine or bromine, and most preferably bromine, and wherein Z is as defined above, e.g., to provide a prenyl, geranyl, solanesyl, phytyl or like group. The prenyl-type compound may be substituted with one or more hydrocarbyl groups in place of a hydrogen bonded to a carbon atom. The hydrocarbyl-containing group may be, for instance, alkyl of from 1 to about 30 carbon atoms. The prenyl component is preferably of trans configuration to a major extent and most preferably is substantially entirely of this structure. The prenyl alkylation reaction proceeds at room temperature. The temperature employed during this reaction may be lower or higher than ambient temperature, but generally may be about 5° or 10° C. to about 50° or 60° C., preferably about 15° to 35° C. The reaction is preferably conducted under non-acidic conditions and can be performed in an inert atmosphere which conveniently may be nitrogen. It is desirable that the prenylation reaction be conducted in the presence of an inert, liquid, organic solvent in an amount sufficient to dissolve the reactants, and it has been found that non-polar, hydrocarbon-containing solvents or protic solvents favor prenylation at the desired carbon atom, whereas prenylation of the oxygen function at the salt position of the substituted naphthol component may occur with highly aprotic solvents. Preferred solvents are anhydrous hydrocarbon solvents such as benzene, toluene, xylene, naphthalene, and the like.

In the reaction between the alkali metal salt of the 3-alkyl-4-alkoxy or aralkoxy-1-naphthol and the prenyl halide, a molar ratio of the naphthol salt to prenyl halide may be about 1:10 to 10:1, preferably bout 2:1 to 1:2. The solvent may be provided in amounts of about 1:1 to 1000:1, preferably 25:1 to 500:1, times the weight of the naphthol salt. The reaction may take up to 50 hours or more, but is often complete in about 0.5 to 30 hours. The reaction is preferably conducted under anhydrous conditions.

The prenyl alkylation reaction yields products which can be oxidized to the corresponding prenyl-substituted menaquinones. This method of synthesizing the prenyl-substituted menaquinones provides these products in high yields and with the maintenance of th stereoconfiguration of the prenyl reactant to a great extent and the prenyl substituent may be substantially entirely of the same configuration as in the prenyl halide reactant.

The prenylated naphthalenes which are obtained in accordance with the method of this invention have oxygen functions at the 1 and 4-carbon positions of the naphthalene nucleus. Keto functions at the 1 and 4-positions, i.e., the corresponding menaquinones, can be obtained without undue adverse effect on the prenyl substituent, by subjecting the prenylated naphthalene to oxidation. The oxidation is preferably effected by, for instance, using ferric ions as an oxidizing reagent. The oxidation reaction can be conducted in other ways, e.g., by bubbling oxygen through a solution of the prenylated naphthalene or by use of silver (II) oxide (argentic oxide) as an oxidizing agent. The silver (II) oxide may be used in excess in the presence of a strong mineral acid. The oxidation reaction can be conducted in the presence of a liquid organic solvent, e.g., an oxygen-containing solvent such as alcohols, ethers or their mixtures, to place the organic reactant in solution. This reaction is preferably conducted under an inert atmosphere such as nitrogen and under essentially anhydrous conditions, except when argentic oxide is the oxidizing agent, in which case the preferred solvent is a mixture of dioxane and water. The oxidation reaction may proceed at room temperature, although elevated temperatures can be employed. Suitable temperatures may be, for instance, about 20° to 50° C., preferably about 25° to 35° C. Generally, the oxidation reaction can be performed under relatively mild oxidation conditions.

The recovery of the MK Compounds may be effected by conventional means, for instance, by extraction by petroleum ether and water or aqueous salt solution. Column chromatography using, for instance, kieselgel absorbent, may also be useful.

The MK Compounds may be substituted at one or more of the 5, 6, 7 and 8 positions. Such substituted MK Compounds may be prepared employing a correspondingly substituted structure as the starting material where the substituent is non-reactive during the synthesis of the MK Compound, or the substituent may be appropriately blocked during the reaction and later recovered to obtain the desired substituted MK Compound.

The present invention will be illustrated by the following examples in which the reactions are conducted at room temperature and under a nitrogen atmosphere and all parts and percentages are by weight, unless otherwise noted.

To a mixture of 1.3 grams of 2-methyl-1,4-naphthoquinol-1-acetate and 1.66 grams of potassium carbonate are added 18 milliliters of dry acetone and 1.28 grams of benzyl bromide, and the resulting reaction mixture is refluxed for 24 hours. The solid materials are removed from the reaction mixture by filtration and the solvent phase is evaporated to obtain a residue which is then triturated with petroleum ether (10 ml.) to obtain 1.81 grams of crystalline 2-methyl-4-benzyloxy-1-naphthyl acetate.

To a mixture of 1.76 grams of the 2-methyl-4-benzyloxy-1-naphthyl acetate and 10 milliliters of absolute ethanol is added 10 milliliters of a 2.0 N aqueous potassium hydroxide solution. This mixture is heated briefly at about 100° C. until a complete solution is achieved. The mixture is then cooled and neutralized with about 20 milliliters of 1.0 N hydrochloric acid to yield a fluffy precipitate containing 2-methyl-4-benzyloxy-1-naphthol which is recovered by filtration (crude yield of 1.43 grams).

A mixture of 1.38 grams of the 2-methyl-4-benzyloxy-1-naphthol, 1.45 grams of anhydrous potassium carbonate, and 16 milliliters of dry acetone is prepared. To this mixture is added 1.49 grams of methyl iodide, and the resultant mixture is refluxed for 14 hours. On completion of the reaction, 50 milliliters of petroleum ether are added, and the resultant salts are removed by filtration. The filtrate is evaporated and the residue is dissolved in 1 milliliter of benzene and 20 milliliters of petroleum ether are added to resolve 1-methoxy-2-methyl-4-benzyloxynaphthalene by crystallization. Crystallization occurs at 4° C. to yield 1.23 grams of the product.

The 1-methoxy-2-methyl-4-benzyloxynaphthalene, in an amount of 925 milligrams, is added to a mixture of 286 milligrams of a 10 percent palladium/carbon catalyst in 20 milliliters of ethyl acetate. The resultant mixture is subjected to hydrogenolysis by contact with a mixture of hydrogen and nitrogen at atmospheric pressure for 38 hours. Subsequent to the hydrogenolysis, the catalyst is removed by centrifugation, and the crude product is obtained by solvent evaporation. Crystallization of the product from benzene/petroleum ether gives 4-methoxy-3-methyl-1-naphthol in an amount of 473 milligrams.

A mixture of 83 milligrams of 4-methoxy-3-methyl-1-naphthol, 17.6 milligrams of potassium hydride and 1.6 ml. of toluene is stirred under nitrogen at 110° C. until hydrogen evolution ceases (about 1 hour). The mixture is cooled to room temperature and 87 milligrams of trans-geranyl bromide added. The resulting mixture is stirred for 24 hours while reaction ensues. The reaction mixture is then diluted with about 5 ml. of petroleum ether, and precipitated salts are removed by centrifugation. The solvents are then evaporated, and under nitrogen 1 ml. of ethyl ether, 1 ml. of 95% ethanol and 1 ml. of 1M aqueous ferric chloride are added sequentially. The resulting heterogeneous reaction is stirred for 15 minutes and then partitioned between petroleum ether and water. The organic phase is evaporated and the product is chromatographed (5% ethyl ether/petroleum ether) to yield 55 milligrams of crude 3-geranyl-2-methyl menaquinone (96%-trans).

The corresponding 3-prenyl-substituted-2-methyl menaquinones can be prepared by substituting of trans-geranyl bromide in the foregoing alkylation reaction an equivalent amount of prenyl, solanesyl or phytyl bromide. The resulting products can be oxidized with ferric chloride in the same manner as indicated in th foregoing example to prepare the corresponding 3-prenyl-substituted-2-methyl menaquinones. For example, phylloquinone can be made via alkylation of the potassium salt of 4-methoxy-3-methyl-1-naphthol with phytyl bromide followed by oxidation in accordance with the following procedure. The 4-methoxy-3-methyl-1-naphthol (83 mg., 0.45 mmol) and KH (0.45 mmol) under nitrogen in 2 ml. of toluene are stirred together at 110° C. until $H_2$ evolution ceases, which takes about 1 hour. After cooling to room temperature, phytyl bromide (0.40 mmol) is added and the reaction mixture is stirred for 24 hours as the reaction proceeds. The reaction mixture is diluted with petroleum ether (5 ml.), the salts are removed by centrifugation, the solvents are evaporated, and, under nitrogen, ethyl ether (1 ml.), 95% ethanol (1 ml.) and aqueous ferric chloride (1.0M, 1ml., 1 mmol) are added sequentially. The resulting mixture is stirred for 15 min. and then partitioned between petroleum ether and water. The organic phase is evaporated and the crude product is chromatographed (5% ethyl ether/petroleum ether) to yield phylloquinone, 53%, all-trans.

It is claimed:

1. A method of preparing 1-naphthol of the formula

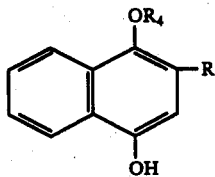

wherein R is lower alkyl and $R_4$ is lower alkyl, comprising alkylating with a benzyl halide alkylating agent of 7 to about 10 carbon atoms 1-acylated-1,4-naphthoquinol of the formula

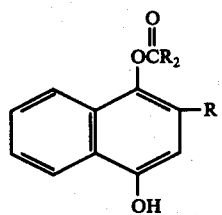

wherein $R_2$ is lower alkyl to produce ether-ester of the formula

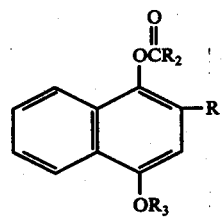

wherein $R_3$ is a benzyl of 7 to about 10 carbon atoms, hydrolyzing said ether-ester to naphthol of the formula

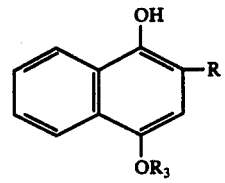

, alkylating said naphthol with a lower alkyl halide alkylating agent to form a diether of the formula

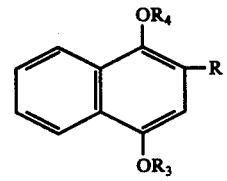

, and hydrogenolyzing said diether at a temperature of about 15° to 100° C. in the presence of a platinum group metal catalyst to form the corresponding 1-naphthol of the formula

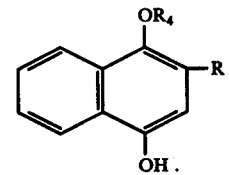

2. The method of claim 1 wherein R is methyl.
3. The method of claim 2 wherein $R_2$ and $R_4$ are methyl.
4. The method of claim 3 wherein $R_3$ is benzyl.

* * * * *